(12) United States Patent
Skinner

(10) Patent No.: US 8,329,435 B2
(45) Date of Patent: Dec. 11, 2012

(54) METHODS FOR IMPROVED UPTAKE OF BIOLOGICAL MOLECULES

(75) Inventor: Keith K. Skinner, Denver, CO (US)

(73) Assignee: American Symbolic, LLC, Las Vegas, NV (US)

( * ) Notice: Subject to any disclaimer, the term of this patent is extended or adjusted under 35 U.S.C. 154(b) by 0 days.

(21) Appl. No.: 12/890,451

(22) Filed: Sep. 24, 2010

(65) Prior Publication Data

US 2011/0015372 A1    Jan. 20, 2011

Related U.S. Application Data

(62) Division of application No. 11/769,548, filed on Jun. 27, 2007, now abandoned.

(51) Int. Cl.
C07K 5/037 (2006.01)
(52) U.S. Cl. .................................. 435/129; 530/207
(58) Field of Classification Search ................. None
See application file for complete search history.

(56) References Cited

U.S. PATENT DOCUMENTS

| | | | |
|---|---|---|---|
| 6,620,419 B1 | 9/2003 | Lintner | |
| 7,118,746 B1 | 10/2006 | Naughton et al. | |
| 2004/0147452 A1* | 7/2004 | Yu et al. | 514/18 |

FOREIGN PATENT DOCUMENTS

| | | |
|---|---|---|
| WO | WO 2004022099 | 3/2004 |
| WO | WO 2004032862 | 4/2004 |

OTHER PUBLICATIONS

Caplan, A.I. & Dennis, J.D. 'Mesenchymal Stem Cells as Trophic Mediators,' J. Cell. Biochem, Aug. 2006, vol. 98, pp. 1076-1084.
International Search Report; dated May 19, 2008, from the Korean Intellectual Property Office.

* cited by examiner

*Primary Examiner* — Robert A Zeman
(74) *Attorney, Agent, or Firm* — Eric L. Lane; McKenna Long & Aldridge LLP

(57) ABSTRACT

A "one-step" process for production of peptides and other organic molecules which are both esters and also acetylated forms of the desired molecule. The ester may be a mono-ester, di-ester, or another poly-ester, complexed with a molecule for protecting the organic molecules in the digestive tract. The method allows simple adjustment of the delivery properties of the peptides produced, in particular adjustment or addition of lipiphilic tendencies. A therapeutic or nutrient made by this method comprises acetylated organic molecule esters, in particular an acetylated peptide ester or even an acetylated amino acid ester and demonstrates improved metabolic properties leading to increased efficiency for therapeutic and cosmetic purposes including oral, transdermal, sublingual, buccal, and topical administration. The present disclosure further teaches several specific examples of acetylated esters, including acetyl-glutathione-ester (mGSH), MCAR (carnosine), pyruvate and others modified from base forms by the methods of the present disclosure.

7 Claims, 2 Drawing Sheets

METHODS FOR IMPROVED UPTAKE OF BIOLOGICAL MOLECULES

RELATED APPLICATIONS

Figure 1:
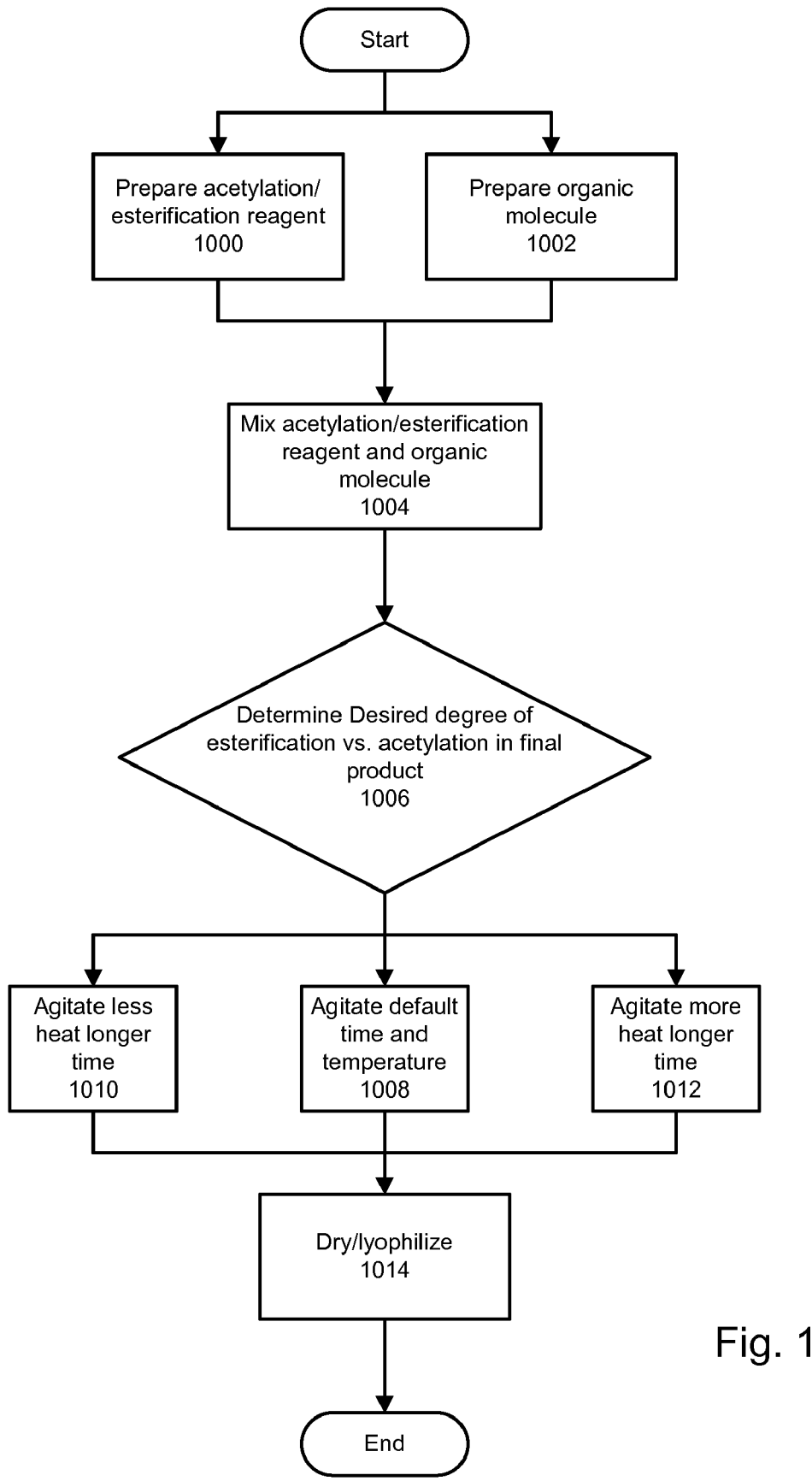

This application is a divisional application of and claims the Paris Convention Priority of and fully incorporates by reference U.S. Utility application Ser. No. 11/769,548, filed on Jun. 27, 2007 now abandoned.

BACKGROUND

This invention relates generally to a method of modifying therapeutic organic molecules and specifically to making biologically effective forms for delivery of peptides.

The cellular activity of therapeutics, nutrients, and therapies in general is an extremely important criteria governing the efficacy of new therapeutics. While there are certain classes of therapeutics which may function well in the intestinal tract or the blood stream, most therapeutics are only truly biologically effective if they are efficient at passing from the stomach into the blood, through the blood stream, and entering the cell.

In general, therapeutics may be considered at several levels of abstraction. Some therapeutic substances may be non-organic molecules and metals that are occasionally used in therapy. In general, however, organic molecules comprise the large majority of therapeutic compounds. The present disclosure relates generally to methods of modifying organic molecules to more effectively pass through the stomach and blood stream to enter cells.

SUMMARY

A "one-step" process for production of peptides and other organic molecules which are both esters and also acetylated forms of the desired molecule. The ester may be a mono-ester, di-ester, or another poly-ester, complexed with a molecule for protecting the organic molecules in the digestive tract. The method allows simple adjustment of the delivery properties of the peptides produced, in particular adjustment or addition of lipiphilic tendencies. A therapeutic or nutrient made by this method comprises acetylated organic molecule esters, in particular an acetylated peptide ester or even an acetylated amino acid ester and demonstrates improved metabolic properties leading to increased efficiency for therapeutic and cosmetic purposes including oral, transdermal, sublingual, buccal, and topical administration. The present disclosure further teaches several specific examples of acetylated esters, including acetyl-glutathione-ester (mGSH), MCAR (carnosine), pyruvate and others modified from base forms by the methods of the present disclosure.

According to a feature of the present disclosure a method is disclosed comprising protecting one or more functional groups of a therapeutic agent to prevent degradation of the therapeutic agent in the bloodstream, associating the therapeutic agent with a protecting agent to prevent degradation in the digestive tract, wherein the protection of the functional groups increases the hydrophobicity of the therapeutic agent to more readily induce absorption of the therapeutic agent through the cellular membrane.

DRAWINGS

Figure 2:
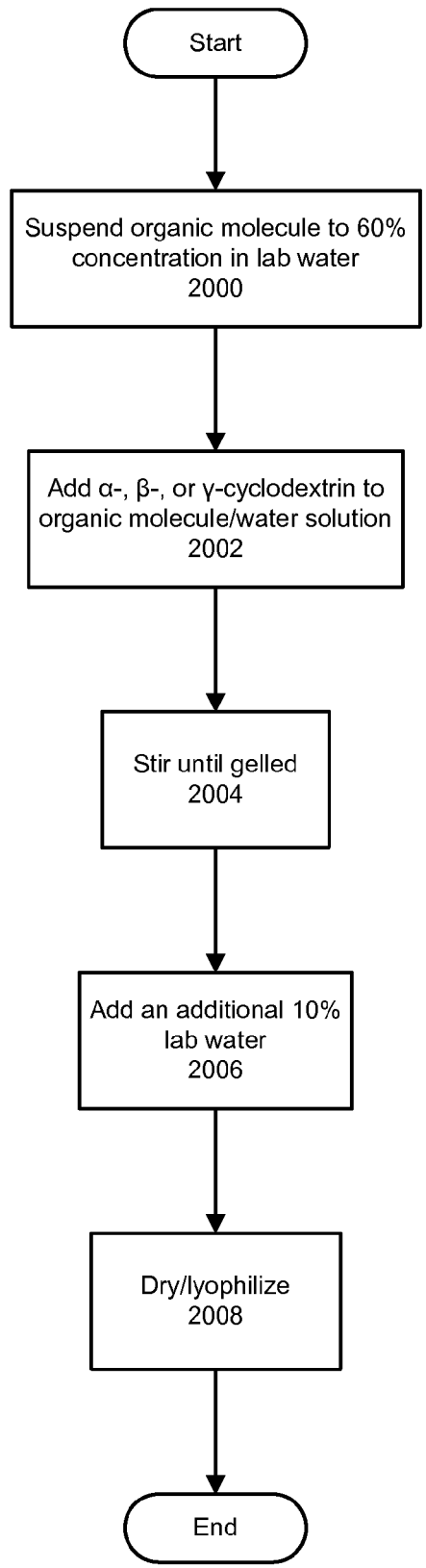

The above-mentioned features and objects of the present disclosure will become more apparent with reference to the following description taken in conjunction with the accompanying drawings wherein like reference numerals denote like elements and in which:

FIG. 1 is a flow diagram of an embodiment of the methods of the present disclosure for acetylating and esterifying organic molecules; and FIG. 2 is a flow diagram of an embodiment of the methods of the present disclosure for adding cyclodextrin to organic molecules.

DETAILED DESCRIPTION

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, biological, electrical, functional, and other changes may be made without departing from the scope of the present invention. The following detailed description is, therefore, not to be taken in a limiting sense, and the scope of the present invention is defined only by the appended claims. As used in the present disclosure, the term "or" shall be understood to be defined as a logical disjunction and shall not indicate an exclusive disjunction unless expressly indicated as such or notated as "xor."

Modification of organic molecules is an unpredictable art in which results may be different from expectations and methods of modifying organic molecules of necessity become very complex. The method of the present disclosure, however, is straightforward and yet yields effective forms of the molecules.

The applications have discovered a novel method for modification of organic molecules. The process involves two steps, as demonstrated by an exemplary embodiment where glutathione is the organic molecule. It will be generally understood that glutathione is representative of many organic molecules, each of which can be substituted for glutathione without undue experimentation.

Glutathione is a three amino acid peptide chain consisting of glycine-cysteine-glutamic acid. It is a potent antioxidant. Thus, intracellular delivery of glutathione is highly desirable from the standpoint of health maintenance. However, as a peptide, glutathione is subject to the proteases of the digestive tract. Moreover, glutathione has a half-life of about a minute and a half in the blood stream.

According to an exemplary embodiment using glutathione, the glutathione molecule is first stabilized by acetylation and esterification to the three active sites of the glutathione molecule, preventing enzymatic degradation in both the digestive tract and the blood stream. A benefit of the stabilization process described herein is that the number of hydrocarbons in the glutathione molecule is reversibly increased, which makes the glutathione molecule more hydrophobic and increases the ability of the molecule to be absorbed through the lipid rich cellular membrane.

The method of the present disclosure alters certain binding sites on glutathione molecules to stabilize the glutathione molecule and prevent degradation prior to entering a cell. Moreover, the present disclosure discloses the use of "protector" molecules designed to effectively deliver through the digestive system modified glutathione molecules into the bloodstream.

Similarly, the hydrogen atom in the amino group may serve as a connection for alteration of the amino acid in a different manner, acetylation of the molecule into a different altered form, which altered form again alters the processes involved in metabolization of the molecule. Adding an acetyl group to either end will begin to render the molecule more likely to pass through early stages of metabolization and thus more likely to finally penetrate the cells.

The method and process of the present disclosure is not limited to amino acid molecules (nor even peptides). For explanatory purposes, however, it will be understood that the connections discussed above may be available in peptides and even in larger proteins, so the same effects are discussed in terms of virtually any peptide/protein of similar structure or other organic molecules having carboxyl, sulphydryl, amine groups, and other active groups subject to acetylation or esterification.

According to embodiments, FIG. 1 illustrates a process for acetylating and esterifying organic molecules, glutathione for example. At operation 1000 and according to embodiments, an acetylation reagent is prepared using 20 μL acetic anhydride and 60 μL of an alcohol or other suitable agent. The alcohol or suitable agent is methanol, ethanol, dimethyl formamide (DMF) and combinations thereof, as well as other suitable alcohols, according to embodiments. Acetylation using methanol and ethanol respectively may lead to the formation of methyl esters and ethyl esters. In proteins, glutathione for example, using DMF may lead to acetylation of either the N-terminal end of the molecule or the N-terminal end and the cysteine terminus.

At operation 1002, up to 1 nmol of an organic molecule, such as glutathione, is reconstituted in 20 μL of 50 mM of ammonium bicarbonate. According to embodiments, the process may be provided to protect many peptides, including from the group consisting of: glutathione, carnosine, pyruvate, and many others. Similarly, other organic molecules having active sites and the need to be protected in the digestive tracts and blood streams are similarly contemplated including vitamins, minerals, antioxidants, enzymes, proteins, etc.

After the organic molecule is reconstituted, 50 μL of the acetylation reagent and 20 μL of the organic molecule solution are combined and allowed to stand at a first temperature for an hour in operation 1004.

Thereafter, the degree of acetylation is determined in operation 1006. According to an embodiment, the final degree of acetylation depends on the specific experimental conditions. The reaction is thermogenic and thus allows reasonably fine control over the degree of alteration of the organic molecule, in particular, the number of acetyl and ester groups added. According to embodiments, modification occurs at one or all active sites of the exemplary glutathione molecule at the amino terminal end, carboxyl terminal end, the sulphydryl group of the cysteine, and the carboxyl side group of the glutamic acid.

According to embodiments, glutathione may be suspended in an ethanol solvent. Naturally, the carboxyl groups will be esterified by the ethanol. When acetic anhydride is added, acetylation of the amino group and sulphydryl group will occur. Steric hindrance will become a factor as an increased number of the functional groups are either esterified or acetylated. Accordingly, the final result will comprise a solution having glutathione molecules with a varying degree of modification to the functional groups. Some glutathione molecules will have all 4 active sites modified, some with 3 of four, and so forth. Depending on the experimental conditions the acetyl to ester ratio is adjusted. For example, by lowering the pH of the solvent, a higher degree of esterification is observed.

According to embodiments, in operation 1008, agitation (with bubbling nitrogen or mechanical stirring) for 24 hours produces an amino acetylated product. If stirring is carried out for 72 hours, a racemic mixture of amino and sulphydryl acetylation occurs in a mixture of roughly equal parts. Addition of acetic anhydride in a 10 fold ratio (molar) will shift the degree of acetylation from the 50/50 ratio to approximately 20 parts amino acetylation and 80 parts sulphydryl acetylation, in glutathione for example.

Temperature variations may also be used to alter the final form of the product in operation 1012. For example, glutathione at 10° C. above room temperature in an alcohol solvent reduces steric hindrance thus allowing both sides of the molecule to acetylate equally; where DMF is the solvent, the result is a 50/50 mix at 100% acetylation. Similarly, variation in the heating and mixing times, produces varying desirable results that may be determined without undue experimentation. Excessive heat demonstrates one possible disadvantage for glutathione and other sulphydryl containing organic molecules, however, which is bonding at the sulphydryl groups into dimers.

In operation 1010, the ability to fine tune the reaction depending on the desired modification of the organic molecule is illustrated. When temperature is reduced but agitation and heating time increases to 5 days (120 hours), thorough acetylation of the sulphydryl group of cysteine is accomplished.

The final product may be lyophilized or otherwise dried for later use in therapeutic products in operation 1014. As a final product, glutathione molecules that are acetylated and esterified at more sites are preferable because (1) acetylation and esterification protect the glutathione molecule as it is in route to a cellular target and (2) the increased molecular weight increases hydrophobicity and makes the molecule more readily absorbed through cellular membranes.

Accordingly, also disclosed by the present disclosure is a method for delivering a therapeutic agent into a cell when administered orally or topically. Although the principles disclosed herein are applicable to many molecules as will be known and understood by artisans, glutathione is again used by way of illustration.

According to embodiments, glutathione is modified by acetylating and esterifying the functional groups of the glutathione molecule, as described herein, for example. Such modification of the functional groups of glutathione prevents enzymes from degrading glutathione in the bloodstream.

Thereafter, according to embodiments, the organic molecule is further protected to allow delivery the molecule through the digestive tract to the large intestine. According to embodiments, each glutathione molecule is placed into a cyclodextrin "bucket." Accordingly, the amino end of the glutathione molecule is held in the cycledextrin ring via eletrostatic forces (as the inner portion of the cyclodextrin ring in more hydrophobic). As the ring resides on the amino terminal end of the glutathione molecule, proteases secreted in the digestive tract are unable to degrade the peptide bonds. Once in the large intestine, cyclodextrin is naturally degraded and the glutathione is absorbed through the wall of the large intestine into the blood stream.

According to embodiments and as illustrated in FIG. 2, complexation of the organic molecule with cyclodextrin is accomplished by suspending the organic molecule to a 60% concentration of lab water (purified and filtered to 0.2 micron, millipore) in operation 2000. This equates to 600 mg/ml by weight. Alpha, beta, or gamma cyclodextrin is added to the organic molecule/water mixture in operation 2002. The mixture is slow stirred for 24 hours until a gel consistency is formed in operation 2004. The gel formation is indicative of complexation of the organic molecule with cyclodextrin. Large vessels are chosen, as this complex swells overnight at a ratio of 1 ml increase in total volume per 1 mg of cyclodextrin used. This gel is then re-diluted with an additional 10% water to give a slurry in operation 2006. This consistency is now kept at room temperature and prepped for spray drying, lyophillization, or vacuum shelf drying in operation 2008. For large scale production, spray drying is appropriate.

According to embodiments, other agents may serve a similar function to that of cyclodextrin, namely: Eudrait RS 100 microparticles. Additionally, according to embodiments, Gliadin may be used to increase uptake of the glutathione molecules from the digestive tract into the bloodstream. A number of compounds are known which act like coatings or containers for the molecules. This group includes, but is not limited to, the use of cyclodextrin, microspheres, nanoparticles of the proper types and properties, and similar compounds, coatings, and containers now known or later discovered.

Other compounds may also increase delivery and penetration. Chitosan is known to bind to the mucosal layer of the intestinal wall, thus preventing the layer from binding to the delivered molecule and thus allowing the delivered molecule to have a better chance of success in penetration. The action of Gliadin and methylcellulose is analogous to cyclodextrin, as these compounds bind to branches of the organic molecule and thus protect that branch from enzymatic attack or the like. Liposomes may provide the molecules of the invention with an additional layer of fat around the molecule, thus further increasing the lipophilic tendencies of the molecule, again making cell wall penetration more likely. In general, enteric coatings of any type, known or later developed, may be used to prevent or reduce enzymatic attack in the digestive tract.

Laboratory tests on this method have been carried out by applying cyclodextrins to acetylated glutathione esters in order to further increase efficiency of delivery and penetration. Wacker Chemical Co. of Adrian, Mich. provides a product named "Cavamax W8" (trademark of Wacker Chemical Co., not related to the present applicants) which brand of cyclodextrin has been used in testing.

Once in the bloodstream, the presence of the acetyl and ester groups prevent degradation of the glutathione molecule in the bloodstream. For example, because the half-life of glutathione in the blood is relatively short—around 120 seconds—modification of the functional groups extends the half-life considerably as it travels to a cell for uptake by the cell. Because the cellular membrane is hydrophobic, the modification makes the glutathione molecule more hydrophobic, which helps the glutathione molecule pass through the cellular membrane.

Referring still to the exemplary embodiment, when such a glutathione molecule is provided which has been more heavily altered with the addition of two, three or even four acetyl groups (a total acetyl group weight gain of +42 over the preexisting weight of the organic molecule per acetyl group added) it becomes fat soluble, and thus less prone to linger outside of the cell, as water soluble peptides/proteins such as glutathione in their natural form are not conveyed into the cell efficiently. This further increases the ability of the molecule to form a useful cream, oil or emulsion, depending on form, thus increasing its suitability for dermal application. As glutathione has been shown to be of benefit in skin cell rejuvenation and thus wrinkle reduction, such an application is very desirable for such purposes.

Once inside the cell, the acetyl and ester groups are naturally cleaved. Thus, active glutathione molecules are delivered inside of a cell without degradation in the digestive tract or bloodstream.

According to embodiments, glutathione forms having only one or two added acetyl groups may be more useful in powder form, as one example. Oral application allows use for other purposes by the metabolism of the patient, yet the addition of the acetyl groups still allows the peptide to penetrate the cells with much greater efficiency than would otherwise be the case.

Certain of the organic molecules of interest, for example, glutathione, may act on the intestinal wall to relax the binding proteins in the paracellular interstices and thus increase penetration of the intestinal wall.

Additional methods for increasing the efficacy of the molecules, in particular by increasing the efficiency of delivery and penetration, are also available for use with the method of the invention.

Methods of delivery of the peptides to be delivered may thus be varied by adjusting the penetration aids discussed and by adjusting the lipophilic/hydrophilic balance of the molecule. As a result, sublingual delivery, oral delivery, cutaneous delivery, subcutaneous delivery, direct bolus delivery, IV drip delivery, and other methods are contemplated.

Another method of delivery is to use a small strip or other body of material which may dissolve in the mouth of the patient. This allows a solid form of the therapy but has the advantages of sublingual or mucosal delivery. In particular, the enzymes of human saliva are only capable of dissolving carbohydrates, not of breaking down proteins or peptides or in fact most types of organic molecules. This means that the first three barriers discussed herein, the enzymatic attack in the stomach, the mucous barrier of the intestinal wall, and the intestinal wall itself, may all be entirely circumvented. However, the patient convenience of having a portable, solid form, exact dosing mechanism is preserved.

Another method of delivery is the transdermal application of molecules, not just peptides and proteins but even single aminos, for effective use not just by the skin or in a topical fashion but actually for use systemically or by other organs of the body. As the present disclosure allows a peptide (or other organic molecule, amino, etc) to be applied dermally and yet absorbed effectively and possibly transported elsewhere. For example, it may be possible to dermally apply a therapeutic for use by the brain, the muscles, vital organs. etc.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method comprising:
   acetylating and esterifying an antioxidant to prevent degradation in at least one of the digestive tract and bloodsteam, including the steps of:
   suspending the antioxidant in an ethanol solvent such that one or more carboxyl groups are esterified by the ethanol;
   adding acetic anhydride to the antioxidant to acetylate one or more amino groups and one or more sulphydryl groups; and complexing a cyclodextrin molecule with the antioxidant to prevent degradation in the digestive tract.

2. The method of claim 1, wherein the antioxidant is glutathione.

3. The method of claim 2, wherein at least three of the amino functional group, sulphydryl functional group, terminal carboxyl functional group, or side carboxyl functional groups are esterified or acetylated.

4. The method of claim 3, wherein all of the functional groups of the glutathione are esterified or acetylated.

5. A method comprising:
protecting one or more functional groups of glutathione by acetylating and esterifying the functional groups to prevent degradation of the glutathione in the bloodstream including the steps of:
suspending the antioxidant in an ethanol solvent such that one or more carboxyl groups are esterified by the ethanol;
adding acetic anhydride to the antioxidant to acetylate one or more amino groups and one or more sulphydryl groups; and
associating the glutathione with cyclodextrin to prevent degradation of the glutathione in the digestive tract;
wherein the protection of one or more of glutathione's functional groups increases the hydrophobicity of the glutathione to more readily induce absorption of the antioxidant through the cellular membrane.

6. The method of claim 5, wherein at least three of the amino functional group, sulphydryl functional group, terminal carboxyl functional group, or side carboxyl functional groups are esterified and acetylated.

7. The method of claim 6, wherein all of the functional groups of the glutathione are esterified and acetylated.

* * * * *